United States Patent [19]
Boussignac et al.

[11] Patent Number: 5,964,220
[45] Date of Patent: Oct. 12, 1999

[54] RESPIRATORY ASSISTANCE APPARATUS

[76] Inventors: Georges Boussignac, 1 Avenue de Provence, 92160 Antony; Jean-Claude Labrune, 19A Rue Massenet, 92310 Sevres, both of France

[21] Appl. No.: 08/937,149

[22] Filed: Sep. 24, 1997

[30] Foreign Application Priority Data

Oct. 11, 1996 [FR] France ................................. 96 12424

[51] Int. Cl.⁶ .................................................. A61M 16/00
[52] U.S. Cl. .............................. 128/204.18; 128/200.24; 128/204.24; 128/204.29
[58] Field of Search .................. 128/204.18, 204.21, 128/204.23, 204.29, 200.24, 204.24

[56] References Cited

U.S. PATENT DOCUMENTS

| | | | |
|---|---|---|---|
| 2,931,355 | 4/1960 | Miller et al. ........................ | 128/204.29 |
| 2,934,293 | 4/1960 | Boehme et al. .................... | 128/204.29 |
| 3,575,167 | 4/1971 | Michielsen et al. ................ | 128/200.24 |
| 4,481,944 | 11/1984 | Bunnell ............................... | 128/204.18 |
| 4,495,946 | 1/1985 | Lemer .................................. | 128/204.25 |
| 4,827,922 | 5/1989 | Champain et al. .................. | 128/204.21 |
| 4,944,292 | 7/1990 | Gaeke et al. ........................ | 128/204.18 |
| 5,107,831 | 4/1992 | Halpern et al. ..................... | 128/204.23 |

FOREIGN PATENT DOCUMENTS

| | | |
|---|---|---|
| 0366524 | 10/1989 | European Pat. Off. . |
| 0097060 | 12/1993 | European Pat. Off. . |
| WO 82/04386 | 6/1982 | WIPO . |

Primary Examiner—John G. Weiss
Assistant Examiner—V. Srivastava
Attorney, Agent, or Firm—Fisher, Christen & Sabol

[57] ABSTRACT

A respitory assistance apparatus which includes:

(a) a plurality of outputs (7.1 to 7.n), each of which can assist one patient;

(b) a plurality of links (8.1 to 8.n) which respectively connect a respiratory gas source to one of the outputs of the apparatus;

(c) a plurality of links (9.1 to 9.n) which respectively connect controlled valve means (5), fed with respiratory gas, to one of the outputs of the apparatus, so that each of the outputs of the apparatus receives one link of each of the pluralities; and (d) flow regulator means (10.1 to 10.n) which are mounted on at least some of the links.

10 Claims, 2 Drawing Sheets

RESPIRATORY ASSISTANCE APPARATUS

BACKGROUND OF THE INVENTION

1. Field of the Invention

The present invention relates to respiratory assistance apparatus.

2. Background Art

It is known that apparatus of this type include a respiratory gas source, for example a pressurized gas bottle, a generator, etc., and controlled valve means which are fed by said respiratory gas source and, at their outputs, generate respiratory gas pulses whose period and duration they control.

Known apparatus of this type are individual and only make it possible to assist one patient.

By controlling the controlled valve means, the inhalation duration and the exhalation duration can be successively controlled over time, in accordance with the patient, while maintaining the desired dead times adjusted by an operator.

An individual apparatus of this type, consequently makes it possible to optimize the respiratory assistance to the patient who is connected to it. However, in the event of disasters or serious accidents involving a large number of casualties who simultaneously require respiratory assistance, it is essential to provide as many respiratory apparatus as there are casualties.

This is generally impossible, and so some victims cannot be assisted before they reach hospital. Of course, this endangers their health, and may even cause their death, even though they could have been saved if they could have been given prompt, even if incomplete, respiratory assistance.

It will, however, be noted that document U.S. Pat. No. 4,495,946 which describes a pulsed breathing apparatus of the type given above, mentions that said apparatus can be used for a plurality of patients at the same time, using a single common oxygen source and by virtue of a single controlled valve. It is quite clear that, in this case, the same breathing cycle is imposed on all the patients, which may be harmful or even fatal to some of them, without the possibility of any adjustment other than the used oxygen flow.

BROAD DESCRIPTION OF THE INVENTION

The object of the present invention is to overcome the aforementioned drawbacks, and it relates to an apparatus which can simultaneously provide a plurality of patients with prompt and effective respiratory assistance.

To this end, according to the invention, the respiratory assistance apparatus including a respiratory gas source and controlled valve means which are fed by said respiratory gas source and, at their outputs, generate respiratory gas pulses whose period and duration they control, said apparatus including a plurality of outputs, each of which can assist one patient, and a first plurality of links which respectively connect said controlled valve means to one of said outputs of the apparatus is noteworthy in that it includes a second plurality of links which respectively connect said respiratory gas source to one of said outputs of the apparatus, so that each of said outputs of the apparatus receives one link of said first plurality and one link of said second plurality; and flow regulator means which are mounted on at least some of the links of said first and second pluralities.

Further to respiratory gas pulses, each patient thus receives a constant-pressure respiratory gas flow which makes it possible to maintain a permanent positive pressure in the patients' lungs. Further to the fact that this permanent positive pressure alleviates the effects of the possible uniqueness of breathing rate, it makes it possible:

to keep the pulmonary alvei of the patients open;

expel carbon dioxide from the lungs; and to improve the oxygen supply to the patients.

The quality of the respiratory assistance delivered by the apparatus according to the invention is therefore particularly high.

Said flow regulator means may include, for each output of said apparatus, a first tap and a second tap, which are respectively mounted on the link of the first plurality and on the link of the second plurality which arrive at said output of the respiratory apparatus.

By virtue of an arrangement of this type, it is therefore possible to control both the constant-pressure respiratory gas flow from said source and the flow of said respiratory gas pulses.

As a variant, each of said flow regulator means associated with an output of said apparatus may consist of a so-called "proportional" valve whose input is connected both to the link of the first plurality and to the link of the second plurality which arrive at said output of the apparatus. Indeed, a valve of this type is known to open proportionately to the flow rate which it receives, so that it is particularly suitable for adding said respiratory gas pulses to said constant-pressure respiratory gas flow.

Preferably, said controlled valve means can be adjusted in order to make it possible to modify the period and the duration of said respiratory gas pulses. The apparatus according to the invention can thus be set to a pulse period and a pulse duration which at least approximately suit each of the patients who are being assisted.

In a first, particularly simple, embodiment of the apparatus according to the present invention, said controlled valve means consist of a single controlled value which is common to all the links of said first plurality. The apparatus according to the present invention thus dispenses gas pulses of identical period and duration to all the patients, individual adjustment of the respiratory assistance being performed by using said taps to control the continuous and pulsed gas flows.

It can therefore be seen, in this first embodiment, that the respiratory assistance apparatus according to the present invention is not optimized for each of the patients who are being assisted, but it allows a plurality of patients to be provided with respiratory assistance of a quality which, although being a compromise, keeps said patients alive until they can receive individual optimized respiratory assistance. Further, it is particularly simple to employ since only the taps for controlling the continuous and pulsed flow rates need to be actuated, so that it can be operated by personnel whose training is fairly rudimentary.

In a second embodiment, which has a high degree of safety and is slightly more complete, said controlled valve means consist of a plurality of individual controlled valves, each of which is mounted on one of said links of the first plurality.

It can be seen that the period and duration of the respiratory gas pulses can thus be tailored to the needs of each of the patients.

The apparatus according to the present invention may include a respiratory gas accumulation reservoir arranged between the respiratory gas source and said controlled valve means.

Similarly, said apparatus may include another respiratory gas accumulation reservoir, arranged between said respiratory gas source and said links of the second plurality.

Said reservoirs thus constitute buffer compartments.

Advantageously, the apparatus according to the present invention includes a plurality of individual components for fitting to patients, for example breathing tubes, breathing masks or the like, each component being fed with gas via one of said outputs of the apparatus. In the case of tubes, they are advantageously of the type described in European patent EP-A-0,366,524.

Moreover, for safety, the apparatus includes a system for measuring pressure which is respectively connected to said individual fitting components. It is thus possible to check that none of the patients has his or her respiratory system subjected to an excessive pressure.

It will moreover be noted that document EP-A-0,097,060 describes a respiratory assistance apparatus which has two outputs on which either a pulsed flow or a continuous flow of respiratory gas are produced.

DETAILED DESCRIPTION OF THE DRAWINGS

The figures of the appended drawing will clearly show how the invention may be embodied. In these figures, identical references denote similar elements.

These figures respectively give a schematic illustration of two example embodiments of the breathing apparatus according to the present invention.

Figure 1:
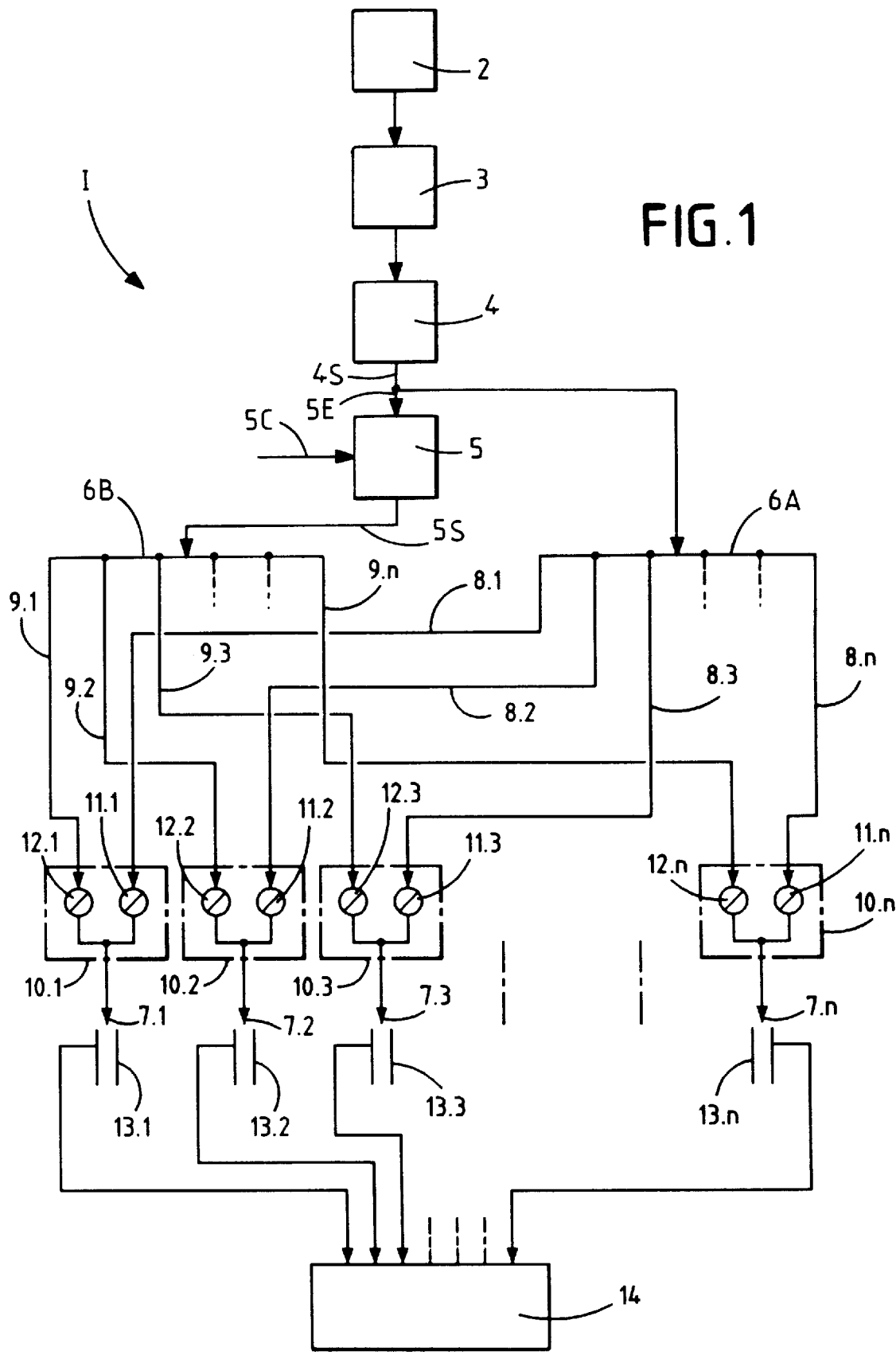
FIG. 1 is a schematic of an embodiment of the breathing apparatus according to the invention.

The breathing apparatus 1 which is shown by FIG. 1 includes a respiratory gas source 2, for example a pressurized gas bottle or a gas generator, optionally associated with a pressure reducer 3. The output of the pressure reducer 3 is connected to an optional reservoir 4.

The output 4S of the reservoir 4 is connected, on the one hand, to the input 5E of a controlled valve 5 and, on the other hand, to a first distribution conduit 6A. The output 5S of the controlled valve 5 is moreover connected to a second distribution conduit 6B.

The controlled valve 5 has a control input 5C, which is connected to a control device (not shown), so that the assembly consisting of the source 2 and the pressure reducer 3 can send respiratory gas pulses to the distribution conduit 6B. The control device controls the valve 5 so that the period and the duration of the respiratory gas pulses can be adjusted.

The respiratory assistance apparatus 1 includes a plurality of outputs 7.1, 7.2, 7.3, . . . , 7.n, each of which is connected via respective links 8.1, 8.2, 8.3, . . . , 8.n and 9.1, 9.2, 9.3, . . . , 9.n, to both the distribution conduit 6A and the distribution conduit 6B. Moreover, flow regulator means 10.1, 10.2, 10.3, . . . , 10.n are mounted on the links 8.1 to 8.n and 9.1 to 9.n in order to regulate the gas exchanges between the distribution conduits 6A and 6B and the outputs 7.1 to 7.n. Each of said flow regulator means 10.1 to 10.n may consist of a proportional valve. However, as a variant, and as shown by FIG. 1, each flow regulator means $10.i$ (with i=1, 2, 3, . . . , n) may include a tap $11.i$ mounted on the corresponding link $8.i$ and a tap $12.i$ mounted on the corresponding link $9.i$.

Each of the outputs 7.1 to 7.n is connected to an individual component 13.1, 13.2, 13.3, . . . , 13.n for fitting to a patient, for example a tube, mask or the like. Thus, by virtue of the control input 5C, it is possible to choose, for all the patients connected to the components $13.i$, the period and duration of the respiratory gas pulses which suit them together. In addition, each of the patients undergoes continuous ventilation by virtue of the continuous respiratory gas stream carried by the distribution conduit 6A. The respiratory assistance is adapted to the situation of each of the patients by controlling the flow rate through operation of the associated taps $10.i$ and $12.i$.

Moreover, a manometer device 14, connected individually to each of the components 13.1 to 13.n, allows the pressure in each of them to be monitored.

Example embodiment II of the apparatus according to the invention, which is illustrated in FIG. 2, again includes the respiratory gas source 2, the pressure reducer 3, the outputs 7.1 to 7.n, the links 8.1 to 8.n, the links 9.1 to 9.n, the flow regulator means 10.1 to 10.n with their taps 11.1 to 11.n and 12.1 to 12.n, the fitting components 13.1 to 13.n and the manometer device 14. However, in this alternative embodiment, the controlled valve 5 which was common to all the lines 9.1 to 9.n has been replaced by a plurality of individual controlled valves 15.1 to 15.n, each mounted on a link 8.1 to 8.n. The controlled valves 15.1 to 15.n each have an individual control input, so that they can be controlled individually by a control device (not shown). The apparatus can thus deliver, at each of its outputs 7.1 to 7.n, respiratory gas pulses whose period and duration are optimal for the patient connected to the corresponding component 13.1 to 13.n.

Figure 2:
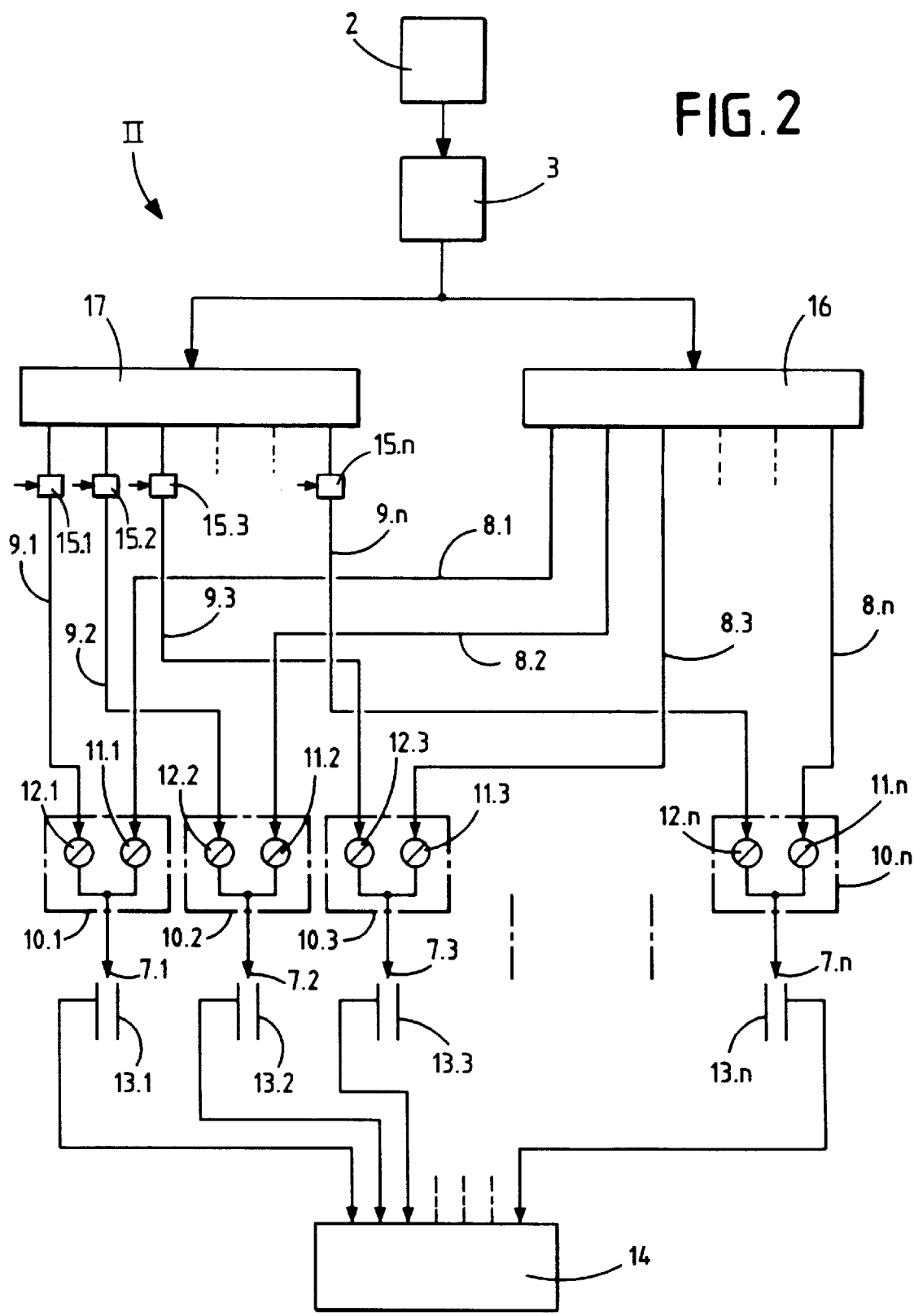
FIG. 2 is a schematic of another embodiment of the breathing apparatus of the invention.

Moreover, in the alternative embodiment II in FIG. 2, the reservoir 4 is replaced by two reservoirs 16 and 17 which are in parallel and each serve as distribution conduits 6A and 6B, all the conduits 8.1 to 8.n being connected to the reservoir 16, and all the conduits 9.1 to 9.n leading from the reservoir 17.

We claim:

1. Respiratory assistance apparatus comprising:

a respiratory gas source;

controlled valve mean, fed by said respiratory gas source and generating respiratory gas pulses, whose period and duration are controlled by said valve means;

a plurality of outputs, each of which can assist one patient;

a first plurality of links, which each respectively separately connects said controlled valve means to one of said outputs of the apparatus;

a second plurality of links, which each respectively separately connects said respiratory gas source to one of said outputs of the apparatus, so that each of said outputs of the apparatus receives one link of said first plurality and one link of said second plurality and a patient connected to one of said outputs of the apparatus can receive respiratory gas pulses and a constant-pressure respiratory gas flow maintaining a permanent positive pressure in his lungs; and flow regulator means, which is mounted on at least some of the links of said first and second pluralities.

2. The respiratory assistance apparatus as claimed in claim 1, wherein said flow regulator means includes, for each output of said apparatus, a first tap and a second tap, which are respectively mounted on the link of the first plurality and on the link of the second plurality which arrive at said output of the respiratory apparatus.

3. The respiratory assistance apparatus as claimed in claim 1, wherein said flow regulator means includes, for each output of said apparatus, a proportional valve whose input is connected both to the link of said first plurality and to the link of said second plurality which arrive at said output of the respiratory apparatus.

4. The respiratory assistance apparatus as claimed in claim 1, wherein said controlled valve means can be adjusted in order to make it possible to set said period and said duration of the gas pulses to a desired value.

5. The respiratory assistance apparatus as claimed in claim 1, wherein said controlled valve means consist of a single controlled valve which is common to all of said links of the first plurality.

6. The respiratory assistance apparatus as claimed in claim 1, wherein said controlled valve means consists of a plurality of individual controlled valves, each of which is mounted on one of said links of the first plurality.

7. The respiratory assistance apparatus as claimed in claim 1, which includes a respiratory gas accumulation reservoir arranged between said respiratory gas source and said controlled valve means.

8. The respiratory assistance apparatus as claimed in claim 1, which includes a respiratory gas accumulation reservoir which is connected, on the one hand, to said respiratory gas source and, on the other hand, to said links of the second plurality.

9. The respiratory assistance apparatus as claimed in claim 1, which includes a plurality of individual components for fitting to patients, each component being fed with respiratory gas via one of said outputs of said apparatus.

10. The respiratory assistance apparatus as claimed in claim 9, which includes a system for measuring pressure which is respectively connected to said individual fitting components.

* * * * *